United States Patent [19]

Fowle

[11] Patent Number: 5,324,286
[45] Date of Patent: Jun. 28, 1994

[54] ENTRAINED CRYOGENIC DROPLET TRANSFER METHOD AND CRYOSURGICAL INSTRUMENT

[75] Inventor: Arthur A. Fowle, Brewster, Mass.

[73] Assignee: Arthur A. Fowle, Inc., Brewster, Mass.

[21] Appl. No.: 6,466

[22] Filed: Jan. 21, 1993

[51] Int. Cl.$^5$ ............................................. A61B 17/36
[52] U.S. Cl. ....................................... 606/23; 606/20
[58] Field of Search ................................... 606/20–26; 62/47.1, 48.1, 50.6, 52.1, 51.1, 500, 490–492

[56] References Cited

U.S. PATENT DOCUMENTS

| | | | |
|---|---|---|---|
| 3,536,075 | 10/1970 | Thomas | 128/303.1 |
| 3,691,784 | 9/1972 | Nicholds et al. | 62/218 |
| 3,800,552 | 4/1974 | Sollami et al. | 128/303.1 |
| 3,910,277 | 10/1975 | Zimmer | 128/303.1 |
| 3,913,351 | 10/1975 | Edwards | 62/402 |
| 3,918,439 | 11/1975 | Zimmer | 128/7 |
| 3,971,383 | 7/1976 | van Gerven | 128/303.1 |
| 4,211,231 | 7/1980 | Rzasa | 128/303.1 |
| 4,295,346 | 10/1981 | Hoffman | 62/500 |
| 4,345,598 | 8/1982 | Zobac et al. | |
| 4,770,171 | 9/1988 | Sweren et al. | 128/303.1 |
| 4,946,460 | 8/1990 | Merry et al. | 606/24 |

FOREIGN PATENT DOCUMENTS

| | | | |
|---|---|---|---|
| 0437377 | 7/1991 | European Pat. Off. | 606/24 |
| 8303961 | 11/1983 | World Int. Prop. O. | 606/23 |

OTHER PUBLICATIONS

Abstract from PCT Publications WO 93/04647, International Application No. PCT/US92/07448, filing date Sep. 4, 1992, *Cryosurgical Instrument with Vent Holes and Method.*

*Primary Examiner*—Stephen C. Pellegrino
*Assistant Examiner*—M. Feffley
*Attorney, Agent, or Firm*—Hamilton, Brook, Smith & Reynolds

[57] ABSTRACT

A cryogenic apparatus comprises a coolant system and a probe having a cryogenically-cooled cold-tip. The probe is formed of an elongated housing having a distal end closed by the cold-tip and a proximal end connected to the coolant system. The housing is adapted to receive cryogenic droplets entrained in a warm carrier gas stream supplied by the coolant system. The carrier gas stream passes through the housing such that the entrained cryogenic droplets are transported to the distal end of the probe for cooling the cold-tip.

24 Claims, 5 Drawing Sheets

ENTRAINED CRYOGENIC DROPLET TRANSFER METHOD AND CRYOSURGICAL INSTRUMENT

BACKGROUND OF THE INVENTION

Cryosurgery is a surgical procedure that uses freezing temperatures to destroy tissue. Its history began in 1865 when James Arnott, an English physician, used this method for the treatment of skin cancer. Modern applications of cryosurgery are numerous. For example, an early cryosurgical apparatus was developed by Dr. Irving Cooper, a New York surgeon, and used for treatment of Parkinson's disease. The apparatus includes an insulated tube or Cannula which has a cold-tip through which liquid nitrogen is circulated. A dime-sized hole is trepanned into the skull to allow for insertion of the cannula. Once the cannula is inserted, the cold-tip is manipulated to destroy a small amount of brain tissue (the thalamus) by freezing it. Starting with the apparatus of Cooper, many modifications for improvement of cryosurgery instruments have been proposed and developed into useful devices. These prior art devices have generally been of two types. One type uses a spray of cold gas and/or liquid applied directly to the tissue to be destroyed; the other uses a closed-end probe wherein a refrigerant is delivered to its distal end cold-tip, which is applied onto or inserted into the tissue to be destroyed. Applications of cryosurgery and the temperature-time histories used in such procedures vary from $-60$ to $-5$ degrees fahrenheit applied for 2 to 5 seconds for repair of a detached retina to near $-320$ degrees fahrenheit applied for several minutes for the destruction of cancerous tumors.

A review of the prior art is presented in U.S. Pat. No. 4,946,460. This patent also describes the current scientific understanding of the process of necrosis (tissue death) by freezing and its translation into the efficacy of programmed control of the temperature history of the target tissue during the freezing processes attendant to specific surgical procedures. In the above and descriptions to follow, the terms cryogenic, cryosurgery, cryogen, etc. are used to reference any temperature which is low with respect to common climatic temperatures. Although among those working in the field of cryogenics, it is common to regard the upper limit of the field to be in the neighborhood of $-240$ degrees fahrenheit, this temperature limit is purely one of choice since there is no single outstanding feature that clearly defines an upper bound.

SUMMARY OF THE INVENTION

The present invention, relating to the improved design of a closed-end cryosurgery probe, embodies two significant advantages over existing state of the art devices. First, the present invention extends the range of applications of cryosurgery medical instruments and techniques to deep within the human body. Currently, the use of cryosurgical instruments is limited to readily accessible body regions because, in existing devices the total length of an instrument's probe, which is inserted into the body and carries a flowing refrigerant, is at about the same temperature as the probe's cold-tip. As such, the use of insulation around the probe along its length is required to protect the tissue through which the probe passes. The requirement for insulation makes the probe diameter relatively large and the probe inflexible which limits its use. The present invention circumvents these limitations of current instruments making possible a probe having a small diameter and a long length having any appropriate degree of flexibility and, hence, allows for the use of a cryogenic probe deep within the human body. The second advantage of the present invention derives from a proposed method for thermal control of the cold-tip temperature which is comparatively simple, reliable and efficient. This method obviates the need to modulate the flow of liquid refrigerant via a flow control valve, a method commonly used in the prior art but one which is relatively less reliable and imprecise. It also substitutes one active control means (heater power) for, in current state of the art methods, the need to supply simultaneously controlled amounts of both heat and liquid refrigerant to the cryotip, which method is inefficient in the use of liquid cryogen and requires larger and more cumbersome dewars for cryogen supply. Finally, the heat capacity of the cooled mass in the proposed device resides in the cryotip region only and is thus much smaller than in conventional designs. This feature results in a much shorter time constant for the temperature responds of the cryotip to control actions than is typical of state of the art designs and, hence, makes possible easier and more precise temperature control.

In the present invention, a cryogenic apparatus includes a coolant system and a probe having a cold-tip for freezing contacted objects such as body tissue. The probe comprises an elongated probe housing having a distal end closed by the cold-tip and a proximal end adapted for receiving a low temperature liquid in droplet form entrained in a warm carrier gas supplied by the coolant system. As the carrier gas passes through an inner passage with the probe housing, the entrained cryogenic droplets are transported to the distal end of the probe housing for cooling the cold-tip.

In one embodiment, the probe housing comprises an inlet tube positioned concentrically within an outlet tube. The inlet tube is connected to the coolant system and passes the entrained cryogenic droplets disposed in the carrier gas to the distal end of the probe. The cryogenic droplets are collected at the distal end of the probe for cooling the cold-tip as described in detail below. The returning carrier gas subsequently passes through an annular region between the inlet and outlet tubes toward the proximal end of the probe for discharge into the atmosphere, Further, the probe housing at the distal end comprises and external tube surrounding the inlet and outlet tubes and connected to the cold-tip. The external tube is formed of a low thermal conductivity material for thermally isolating the inlet and outlet tubes from the cold-tip. As such, the entire length of the outer tube as well as the outer surface of the probe housing at the distal end are near body temperature except in close proximity to the cold-tip.

The cold-tip is cryogenically-cooled by the cryogenic droplets which are collected at the base of the cold-tip. More specifically, the carrier gas transports the entrained cryogenic droplets, through the inlet tube to the distal end of the probe where, because of their inertia, the droplets cannot follow the 180 degree bend of the returning carrier gas stream. Instead, the droplets are deposited and stored in a porous heat sink positioned in the cold-tip. The porous heat sink is positioned such that it is in thermal contact with a cold-tip head. Both the porous heat sink and the cold-tip head are formed of a thermally conductive material. The liquid deposited in the heat sink from impinging droplets is evaporated by heat supplied by the object to be cooled, such as tumor tissue which is placed in contact with the cold-tip head. Accordingly, the cold-tip reaches temperatures commensurate with the saturation temperature of the evaporating liquid cryogen. An optional heater coil may be embedded in the cold-tip for disengaging the cold-tip head from the cooled tissue in a manner employed in many cryosurgical procedures.

The mass flow of the carrier gas is made much larger than that of the liquid droplet stream and, hence, its heat capacity is sufficient to maintain the carrier gas near body temperature even if a substantial fraction of the droplets were evaporated by heat exchange with the carrier gas. The amount of heat exchange between the droplets and carrier gas is limited by the size of the droplets produced in the atomization process, the carrier gas velocities and the Liedenfrost type heat exchange between the droplets and the tube walls that contain them.

The cryogenic apparatus of the present invention includes a cryogenic coolant system for producing liquid cryogenic droplets disposed in a carrier gas. The coolant system comprises a housing having an inlet port and an outlet port. A gas source is connected to the inlet port and supplies the carrier gas to the housing at a controlled temperature and pressure. A condenser post extending into the housing is employed for producing liquid cryogenic droplets. The condenser post is hollow and made of a thermally conductive material. The outer surface of the condenser post is exposed to the carrier gas. The condenser post is kept filled with a boiling cryogenic liquid supplied by gravity flow from an attached dewar which causes the outer surface temperature of the condenser to be less than the saturation temperature of the carrier gas. As such, a cryogenic liquid condensate of the carrier gas forms on the outer surface of the condenser and subsequently drains off and is atomized into droplets. The length and diameter of the condenser post is sized to produce cryogenic liquid condensate at a mass flowrate sufficient to meet the maximum cooling capacity required at the cold-tip. A heater coil is connected to the condenser near its junction with the dewar. The heater coil produces a thermal gradient along the condenser. By controlling the power to the heater coil, the fraction of the total area of the post where condensation takes place can be varied and, hence, the rate of production of the cryogenic liquid condensate and the cold-tip temperature can be controlled simply. The condenser post terminates in a pointed metal tip from which the cryogenic condensate drains into the entrance nozzle to the inner tube of the probe. The condenser post tip and entrance nozzle are suitably shaped and positioned relative to each other to simultaneously produce gas atomized droplets of the desired size and entrain them in the carrier gas stream flowing in the inner tube of the probe where henceforth they are transported to the cold-tip for cooling purposes.

In brief summary, the cryogenic probe apparatus of the present invention is adapted for use in a wide range of surgical procedures including, most importantly, those where the probe must be inserted deep within the human body to freeze a target area without harming the tissue through which it passes. In preferred embodiments, the probe is made of substantially tubular elements up to about four feet in length which have the desirable degree of flexibility and an overall outer diameter of about 2 mm or less. As such, the probe can be easily manipulated for treatment of previously inaccessible or difficult access target areas deep within the human body. Moreover, in a preferred embodiment of the system for supporting the operation of the surgical cryoprobe, the invention advances means and methods for thermal control of the cold-tip temperature which are advantageously simple, reliable and efficient.

BRIEF DESCRIPTION OF THE DRAWINGS

The foregoing and other objects, features and advantages of the invention will be apparent from the following more particular description of preferred embodiments of the invention, as illustrated in the accompany drawings in which like reference characters refer to the same parts throughout the different views. The drawings are not necessarily to scale, emphasis instead being placed on illustrating the principles of the invention.

DETAILED DESCRIPTION OF PREFERRED EMBODIMENTS

Figure 1:
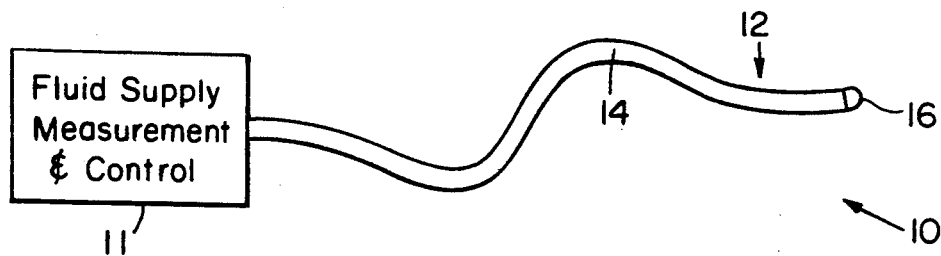
FIG. 1 illustrates generally a cryosurgical apparatus of the present invention.

A cryosurgical apparatus 10 of the present invention is illustrated schematically in FIG. 1. Its major components include a cryogenic cooling system 11 and cryoprobe 12. The cryoprobe 12 comprises a small diameter, flexible, catheter-like tube system 14 with a cryogenically-cooled cold-tip 16 at its distal end. In accordance with the present invention, the outside surface of the probe 12 is near body temperature and the only cold external surface of the probe is the hemispherical cold-tip 16. This important feature is made possible by a novel scheme illustrated in more detail in FIG. 2A.

Figure 2A:
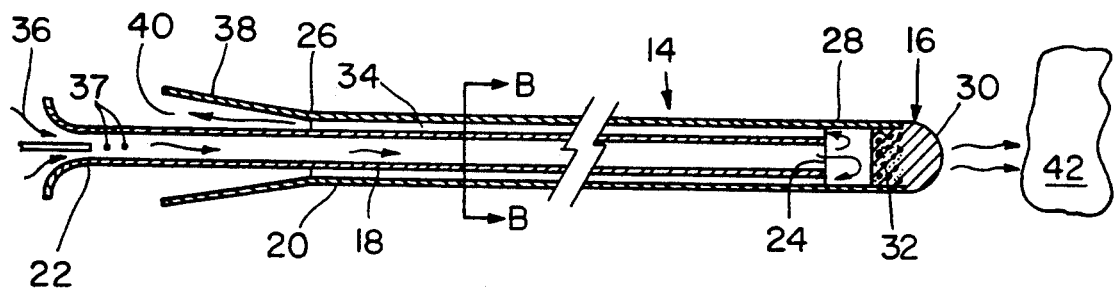
FIG. 2A is a cross-sectional view of a cryosurgical probe embodying the principles of the present invention.
Figure 2B:
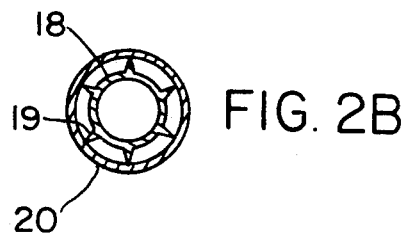
FIG. 2B is a cross-sectional view of the cryosurgical probe of FIG. 2A taken along the line B—B.

FIG. 2A is a cross-sectional view illustrating the cryoprobe's tube system 14 and cold-tip 16. The tube system 14 includes an external spline 19 which positions a central tube 18 concentric with an external tube 20. The external spline 19 is shown in FIG. 2B. The tube system 14 is preferably made from materials which give it the required degree of flexibility and strength for a wide range of surgical procedures deep within a body. For example, a relatively flexible plastic tube system formed by nylon, which may be reinforced, may be employed for particular applications because the walls of the tube system 14 operate near room temperature. Referring back to FIG. 2A, the center tube 18 extends from proximal end 22 to distal end 24 where it terminates just short of the base of the roughly hemispherical cold-tip 16. The external tube 20 is firmly attached to the cold-tip 16 and extends from a proximal end 26 to a distal end 28. The outer diameter of the tube system is made small, preferably about 2 mm or less and its length can be made as long as required up to a limit of about 4 feet. The cold-tip 16 is comprised of a thermally conducting metal head 30 with a porous structure 32 at its base.

In operation of the cryosurgical apparatus 10, a presured dry inert gas stream 36 such as nitrogen is generated by the cooling system 11 (FIG. 1) and flows down the center tube from the proximal end 22 to the distal end 24. The gas stream turns 180 degrees at the cold-tip 16, thus flowing back in the annular space 34 between the central and external tubes toward the proximal end 26 of the external tube. Thereafter, the gas may be channeled through a flow diffuser 38 where it is discharged to the atmosphere at section 40.

In accordance with the present invention, the cooling system also generates droplets 37 of a cryogenic liquid such as nitrogen which are introduced into the gas stream 36 at the proximal end 22 of the central tube 18. The carrier gas stream 36 transports the droplets 37 to the digital end 24 of the central tube where, because of their inertia, the droplet 37 cannot follow the 180 degree bend of the returning gas stream. Instead, the droplets are deposited and trapped on the porous metal base 32 of the cold-tip 16 where they are completely evaporated by the heat supplied by the cooled tissue 42 in the local region around the cold-tip head 30. It is noted that the cryosurgical apparatus employs a carrier gas stream which has a heat capacity large enough to limit the lowest temperature possible in the carrier gas stream to values non-injurious to the tissue through which the catheter-like tube system 14 passes.

Figure 3:
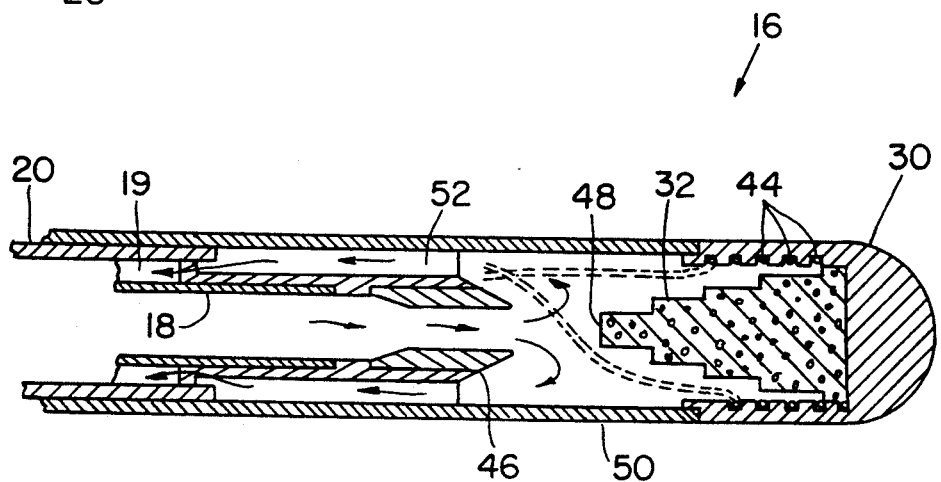
FIG. 3 is an enlarged cross-sectional view of the cold-tip of the cryosurgical probe of FIG. 2A.

FIG. 3 is a detailed illustration of the cold-tip 16 of the probe 12. The head 30 of the cold-tip 16 is formed of a thermally conducting material such as copper. An electrically insulated heater coil 44 is embedded in this head 30. This heater coil is provided to heat rapidly the cryotip 16 as required to disengage it from the frozen tissue at the end of a surgical procedure. Although this heater 44 may be used as an adjunct to the thermal control of the cryotip 16 during the surgical procedure, this is not its main purpose nor is it required for that purpose.

An open-celled metal sponge 32 of cooper or other high thermal conductive material is soldered to the copper cryotip head 30. The sponge 32 traps the impinging liquid cryogen droplets 37 that issue from the nozzle 46 at the end of the inner tube 18 of the annular tube system 14. In a preferred embodiment, this sponge 32 is shaped in a stepped cone- configuration to conform to the heat transfer requirement of the cryotip head 30. When a small mass flow rate of liquid droplets 37 (corresponding to small cooling capacity) leave the nozzle 46 and impinge on the stepped-cone sponge 32, this mass is absorbed near the apex 48 of the cone. Accordingly, the heat extracted from the tissue (not shown) surrounding the cryotip head 30 must flow through a long, increasingly constricted path to the region of the apex 40. In short, this path has an effective thermal resistance that is high, such that the difference between the temperature of the cryotip head and saturation temperature of the evaporating absorbed liquid droplets is large. As the mass flow rate of impinging liquid droplets is increased (corresponding to an increase in cooling capacity), the liquid absorbed by the sponge occupies a larger region about the apex 48. As such, the length of the heat flow path and its degree of constriction becomes smaller. In other words, the effective thermal resistance of the heat flow path is decreased and, therefore, the temperature difference between the evaporating liquid droplets and cryotip head 30 becomes smaller. In this manner, the present invention operates automatically to provide a heat flow path having the variable thermal resistance necessary to match the required steady state condition of larger cooling capacities corresponding to lower cryotip head temperatures.

The central and external tubes 18 and 20 of the annular tube system 14 are connected to and separated from the cold-tip head 30 by a thin-walled isolation tube 50 formed of a material having a low thermal conductivity such as stainless steel. This isolation tube 50 acts as a thermally isolating fin which allows the joints between the cold-tip 16 and the central and external tubes to operate near body temperature regardless of the temperature of the cold-tip head 30. This in turn makes the convenient use of various adhesives such as epoxy formulations at these joints possible. A rugged support for the inner tube and its extension to a nozzle 46 is also provided. This support is attached to the thermal isolation tube via a spider 52 so that the inner tube 18 nozzle bore the outer tube 20 and isolation tube 50 are concentric.

Figure 4:
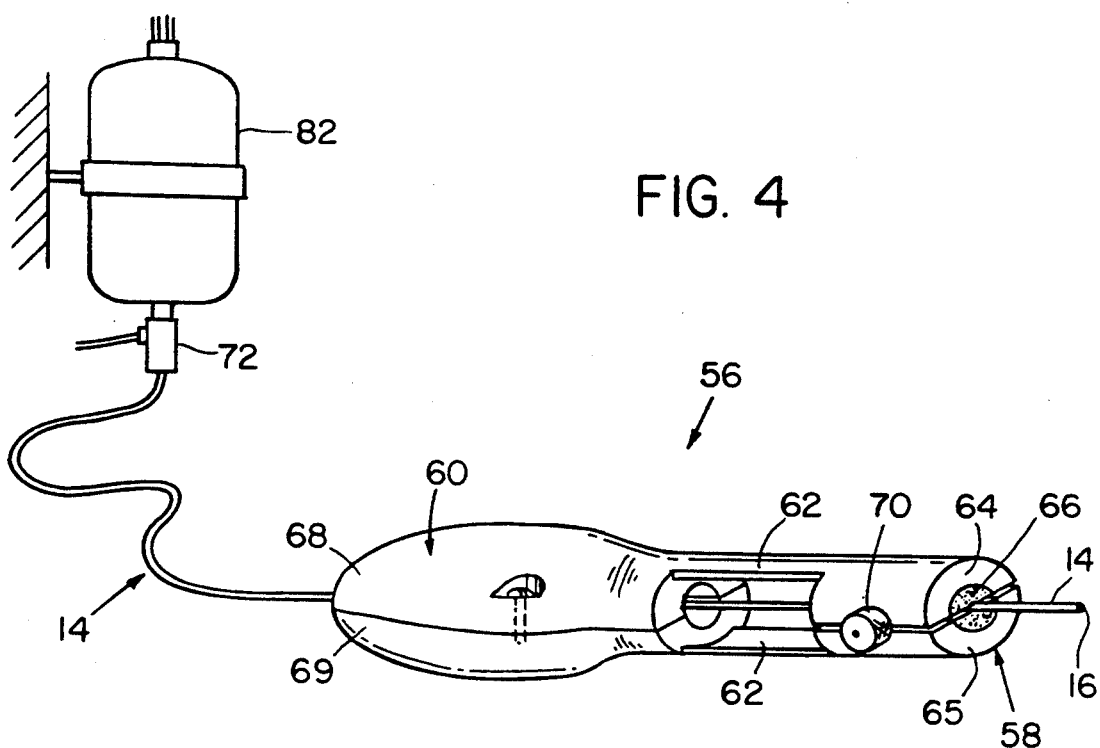
FIG. 4 illustrates a guide tool which facilitates the manipulation of the cryosurgical probe of FIG. 2A.

FIG. 4 illustrates a guide tool 56, which, in the hands of a surgeon, can facilitate the insertion and manipulation of the cryoprobe system including the annular tube system 14 and cryotip 16. The tool 56 comprises a tube clamp 58 connected to a grip 60 by two flexures 62. The clamp 58 has two jaws made by the two halves 64 and 65 of a cylinder with a rubber-filled central hole 66. The grip 60 is also split in two halves 68 and 69 along the same diametral plane as the opposing jaws. This allows the two halves 68 and 69 of the grip and jaws 64 and 68 to be assembled about the cryoprobe tube system 14 and held together by screw connections in the grip halves. After assembly, the cryoprobe tube system 14 becomes effectively threaded through the tool 56, and the tool is free to move axially along the tube system. By squeezing the jaws between thumb and forefinger, the surgeon can clamp the grip to the tube system and, thereby, manipulate it. If a particular and relatively permanent axial position of the tool in respect to the tube system is desired, this position can be secured by a clamp actuated by a rotary knob 70.

As stated previously, the cooling system introduces droplets of a cryogenic liquid into the carrier gas stream which transports the liquid droplets to the cold-tip for cooling tissue adjacent to its metal tip. Referring back to FIG. 2A, some necessary and/or desirable characteristics of the cooling system for a preferred cryosurgical apparatus are as follows:

(1) Supply sufficient flow rate of liquid droplets 37 such that the cold-tip 16 is capable of reaching and maintaining its specified operating temperature. In the present invention, a train of equally spaced and equal size drops on the centerline of the center tube 18 is the ideal manner of droplet insertion at the proximal end 22 of the central tube 18.

(2) Supply sufficient flow rate of a warm carrier gas 36 such that its temperature when returning along the annular space 34 from the distal end 28 to the proximal end 26 of the outer tube 20 is near body temperature.

(3) Generate and introduce liquid cryogenic droplets 37 having a size which limits the amount evaporated in passing from the proximal end 22 to the distal end 24. In preferred embodiments, the droplet size is on the order of about 200 microns in diameter.

(4) Generate and introduce liquid cryogenic droplets 37 having a size which after evaporation will deposit on the porous base 32 cold-tip 16. In most, if not all, cases when criterion (3) is achieved, criterion (4) is also achieved.

(5) Supply the carrier gas 36 at sufficient pressure to provide the required flow rate in the small diameter central tube 18 with a pressure drop that is a small fraction, about 25 percent, of the inlet pressure at the proximal end 22. The configuration of the flow passage between sections 28 and 26 of the outer tube 20 is designed to have a pressure drop of about 75 percent of the inlet pressure. The flow diffuser 38 downstream of the proximal end of the outer tube may be employed to reduce the velocity of the gas existing at section 40 to a small value.

Figure 5:
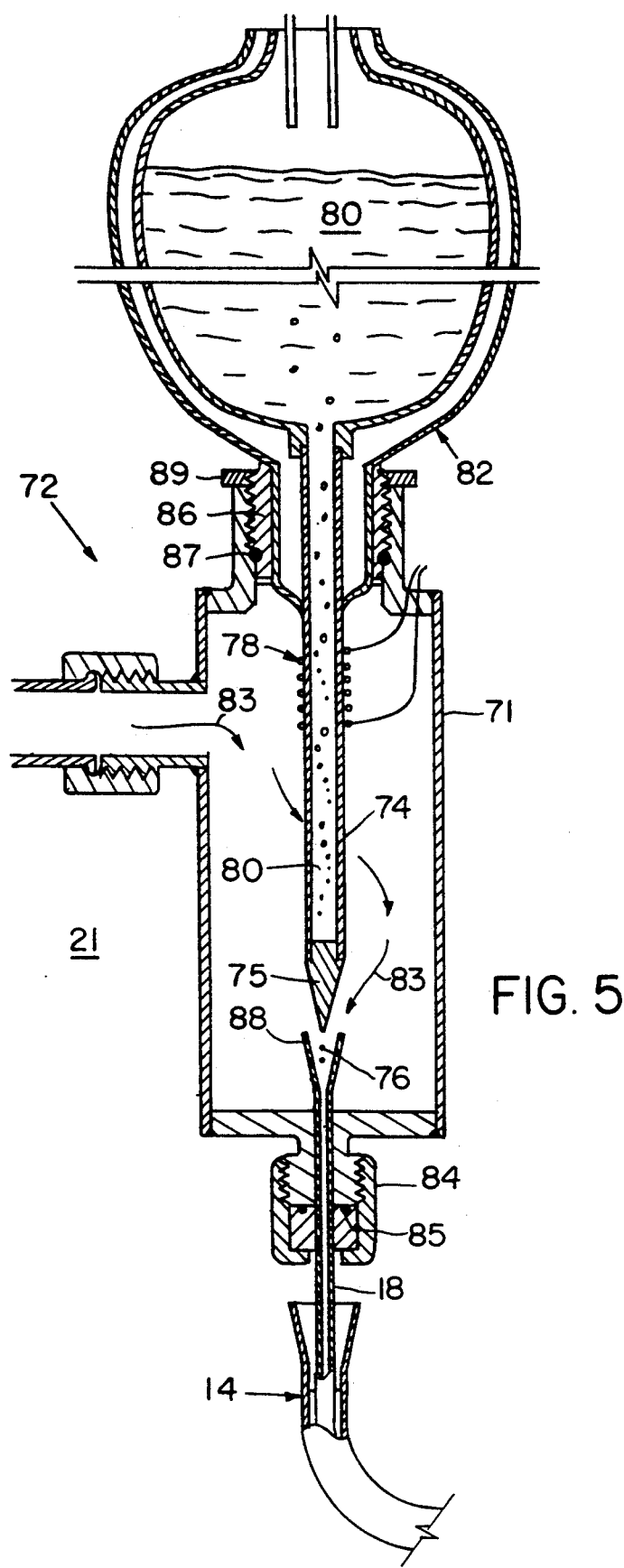
FIG. 5 is a cross-sectional view of a preferred system for producing the cryogenic coolant employed in the cryosurgical apparatus of the invention.

FIG. 5 depicts a preferred cooling system 21 for producing the liquid cryogen in droplet form via atomization by the carrier gas stream. In this embodiment, the system includes cryoprobe head 72 comprising an essentially cylindrical vessel 71 having an inlet for a carrier gas 83 and an outlet 88 to the proximal end of the cryoprobe 14. Vessel 71 is penetrated by a hollow post 74 connected to a cryogenic dewar 82 containing a liquid cryogen 80. The hollow post made of a thermally conductive material such as copper is fed with the liquid cryogen by gravity flow from the attached dewar. A gas source (not shown) is connected to the inlet port of the cryohead and supplies the carrier gas 83 at a controlled temperature and pressure. The pressure of the carrier gas is fixed such that its corresponding saturation temperature is above the boiling point temperature of the cryogen in the dewar. Accordingly, the carrier gas will condense on the post. The latent heat associated with the condensation of the carrier gas will result in the boiling of the cryogen in the post. When the carrier gas and the boiling liquid cryogen in the condenser post are just different phases of the same substance, for instance nitrogen, the conditions for operation are met if the pressure of the carrier gas in the cryohead is elevated above that in the dewar ullage. The condensate film formed on the condenser post will drain from the condenser post at the conically pointed or otherwise suitably shaped metal tip 75 into entrance nozzle 88 where it is subsequently gas-atomized into droplets. The entrance nozzle is conically or otherwise suitably shaped and is positioned centrally and in proper axial relationship to the tip of the condenser post so that the draining condensate is simultaneously gas-atomized by and entrained in the carrier gas stream as droplets having the desired size.

The length and outer diameter of a condenser post 74 is sized to produce a mass of condensed liquid cryogen droplets 76 at a rate necessary to meet the maximum heat extraction rate (cooling capacity) required at the cold-tip (not shown). For example, a post having an outside diameter of approximately 0.15 in. and a length of approximately 3 in. is calculated to meet the majority of the heat capacity requirements when the carrier gas and liquid cryogen in the dewar are both nitrogen. In order to meet desired heat extraction rates less than the maximum amounts, the post 74 is heated by means of a heater coil 78 attached to the upper end of the post. Electric power supplied to the coil 78 heats the upper end of the post 74 while the lower extremity of the post remains near the boiling point temperature of the liquid cryogen 80 in the dewar 82, and, thereby produces a temperature gradient along the vertical post. At locations on the post 74 where the surface temperature is above the saturation temperature of the pressurized carrier gas 83 (most often, but not necessarily, the gas phase of liquid cryogen 80) condensation will be prevented and the mass of production of liquid cryogen droplets 76 and, hence the cooling capacity of the cryotip will be reduced. In this way a very sensitive, simple and reliable means for adjusting the cooling capacity of the cryotip is provided. Moreover, as a simple monotonic relationship between cooling capacity and the temperature of the head of the cryotip exists—that is, an increase in cooling capacity leads to a reduction in cryotip head temperature—a temperature sensor (not shown) mounted in the cryotip head will be sufficient to provide the input signal to a controller (not shown) which, by well-known methods, supplies power to the heater coil in amounts that produce the desired cryotip temperature vs. time profile.

The proposed method obviates the need to modulate the flow of liquid cryogen via a flow control valve which is relatively unreliable and imprecise. It substitutes one active control action (heater power) for, in current state of the art methods, the need to supply both controlled amounts of heat and liquid cryogen to the cryotip, which procedure is relatively inefficient in the use of the liquid cryogen. Also, the time constant for the response of the cryotip temperature to active control actions in the preferred cooling system is very much shorter than in state of the art designs. The reason for this is twofold: 1) the heat capacity or thermal inertia in the proposed system resides in the cryotip only and is, thereby, smaller than that in conventional designs which have a larger cooled mass of material and 2) the imprecise modulation of the liquid cryogen flow which requires a balancing heat addition, introduces the thermal inertia represented by the latent heat of the evaporated liquid cryogen which does not go to cool the cryotip.

Some other useful features of the design of the cryoprobe head 72 illustrated in FIG. 5 are as follows. A coupling 84 and a seal 85 to the cryoprobe tube system 14 is provided so that different systems designed for particular surgical procedures can be used with a single cryohead 72. The threaded connector 86, seal 87 and locknut 89 at the top of the cryoprobe head 72 provide two functions: a) means for attaching the head to the dewar 82 and b) means for adjusting the axial position of the tip 75 of the condenser post 74 in relationship to the entrance nozzle 88 to the inner tube 18 of the annular tube system 14 thereby, controlling the size of the gas-atomized liquid cryogen droplets. The internal volume of the liquid cryogen storage dewar 82 is made large enough to supply all the liquid cryogen 80 necessary for one surgical operation with a single filling. This is estimated at about 20 cubic inches for typical operations using nitrogen as the coolant.

Figure 6:
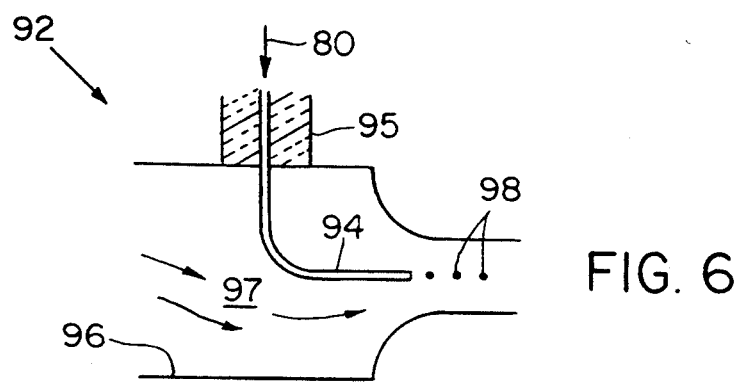
FIG. 6 is a cross-sectional view of an alternative system for producing the cryogenic coolant.
Figure 7:
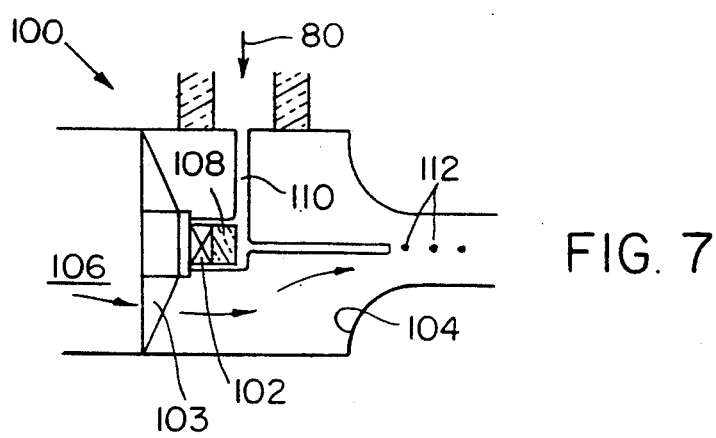
FIG. 7 is a cross-sectional view of another alternative system for producing the cryogenic coolant.

Alternative cooling systems for producing the cryogenic coolant for the present invention are shown in FIGS. 6 and 7. In addition to allowing operation with a variety of carrier gases and liquid cryogens, the embodiments illustrated in FIGS. 6 and 7 provide good control of the atomization and early stage droplet evaporation processes which may prove to be critical. However, these embodiments require that the flow rate of liquid cryogen droplets be modulated by a flow control valve integrated into an overall control system.

FIG. 6 shows a pressurized liquid/gas jet atomizer 92 whose detailed design characteristics are set forth in the prior art. The atomizer 92 employs a liquid jet 94 which extends through thermal insulation 95 and into a volume 96 filled with a carrier gas 97. In preferred embodiments of the invention the required drop size is relatively large, typically about 200 microns, and therefore the relative velocity between gas and liquid at the exit of the liquid jet 94 is made small, of the order of 10 ft./sec., and the diameter of the exit orifice of the jet is made small, of the order of 3 mils. The atomizer 92 produces a stream of liquid cryogen droplets 98 which are transported by the carrier gas 97 to the tube system (not shown).

FIG. 7 shows a sonic-augmented pressurized liquid/gas jet atomizer. In this atomizer a piezoelectric or other sonic transducer 102 is supported by a spider 103 in a volume 104 filled with the carrier gas 106. The transducer 102 is positioned adjacent to thermal insulation 108 in the liquid jet feed stream 110 to pulse this stream to provide droplets 112 with improved control over their size and spacing in the carrier gas stream 106. The transducer 102 is centered in an essentially half wavelength resonant-tube configuration. The appropriate pulse frequency of the transducer 102 is preferably of the order of 10,000 cycles per second.

Figure 8:
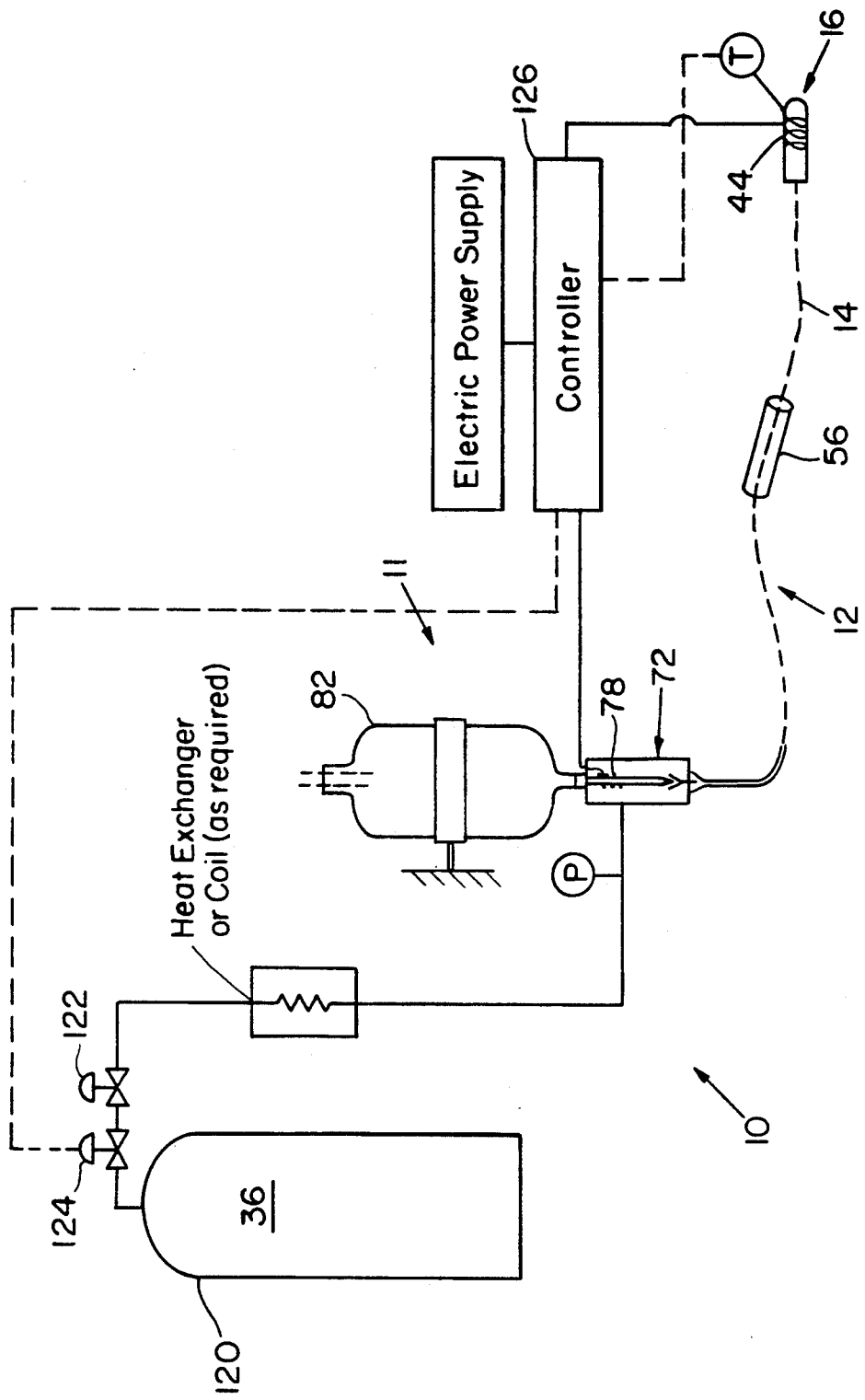
FIG. 8 is a diagrammatic view of the cryosurgical apparatus of the present invention.

FIG. 8 illustrates the major elements of the cryosurgical apparatus and their interrelationship. The carrier gas 36 is supplied to the cryoprobe 12 from a standard high-pressure storage bottle 120 at a predetermined pressure fixed by a pressure regulating valve 122. A solenoid-activated on-off valve 124 is provided to open at the start of the surgical procedure and to close at the end. The cryosurgery apparatus 10 comprising the storage dewar 82, cryoprobe head 72, tube system 14, cryotip 16, guide tool 56, and control means 126, previously described as isolated elements, are depicted in a fully assembled arrangement.

A brief description of the operation of the apparatus is as follows. First, a tube system 14 and cryotip 16 most appropriate to the operational procedure are selected and assembled as shown in FIG. 8. Major variables in the selection process include the length and degree of flexibility of the tube system and the geometric shape of the cryotip head and attached metal sponge. Next, the sequence of operations for start-up and shut-down together with the desired cryotip temperature vs. time history including terminal thawing is fed into the programmable microprocessor/controller 126. Finally, the actuation of a start button (not shown) sets the preprogrammed operational schedule into automatic execution. In preferred embodiments, the microprocessor/controller 126 is designed such that manual adjustments and overrides to the initially programmed schedule can be introduced by the surgeon.

THEORETICAL BASIS FOR THE INVENTION

Probe-Tip/Tissue System Heat Transfer

The following analytical results establish the relationship between the extent of the frozen tissue as dependent on the probe-tip size, heat extraction capability, temperature and time.

1. Probe Tip Heat Transfer in Steady State

For a spherical heat sink (the probe-tip) surrounded by an infinite conductive medium (tissue), it can be shown that the isothermal surfaces surrounding the probe-tip are spheres and that the rate of heat transfer to the probe is given by:

$$q = \frac{4\pi k_s(T_i - T_p)}{\frac{1}{r_1} - \frac{1}{r_2}} = \frac{4\pi K_f(T_\infty - T_i)}{\frac{1}{r_2}} \quad (1)$$

$k_f$ = thermal conductivity of unfrozen tissue
$k_S$ = thermal conductivity of solid frozen tissue
q = rate of heat transfer to probe tip at steady state
$r_1$ = radius of probe-tip
$r_2$ = radius of outer boundary of frozen tissue
$T_i$ = freezing temperature
$T_p$ = probe-tip temperature
$T_\infty$ = temperature of unfrozen tissue far away from probe-tip From the algebraic manipulation of equation 1, the radius ratio is:

$$\frac{r_2}{r_1} = 1 + \frac{k_s(T_1 - T_p)}{k_f(T_\infty - T_i)} \quad (2)$$

As an example of the application of equations 1 and 2, let $k_S$=0.5 BTU/hr-ft-F, $k_f$=0.25 BTU/hr-ft-F, $T_i$=32F (492R), $T_\infty$=98.6F (558.6R) and $r_1$=0.04 inches. In this typical case, $$\frac{r_2}{r_1} = 1 + 0.030(T_i - T_p)$$

and q=0.2043[1+0.030 ($T_i-T_p$)] (watts).

Both $r_2/r_1$ q are linear functions of $T_i-T_p$ and have the magnitudes presented in the table below.

| Typical thermal Characteristics of Cryoprobe Tip Operating at Steady State | | |
|---|---|---|
| $T_p$ (R) | $r_2/r_1$ | q (watts) |
| 144 | 11.44 | 2.34 |
| 200 | 9.76 | 1.94 |
| 300 | 6.76 | 1.38 |
| 400 | 3.76 | 0.77 |

Because the typical probe-tip is hemispherical rather than spherical, the actual value of q may be closer to 60 to 65 percent of that tabulated.

2. Heat Transfer in Cooldown Transient

The thermal behavior of the probe-tip/tissue system during the cooldown transient is needed in order to establish the time required to approach the steady state condition and to provide the theoretical basis for control of the cryosurgical procedure. A rigorous treatment of the cooldown transient is very involved. However, a relatively simple, good approximation to the real case can be obtained by noting that: 1) the time constant for conductive heat transfer is very short (of the order of ten seconds), 2) the change in internal energy of the probe-tip and tissue due to their sensible heats is very much smaller than that due to the latent heat of fusion accompanying the tissue change of phase, and 3) the heat extraction at the probe-tip is a constant value set by its maximum design capability. With these simplifications, the transient heat transfer equation in differential form becomes:

$$q - 4\pi k_f(T_\infty - T_i) = 4\pi h_{sf}\rho r^2 \frac{dr}{dt} \quad (3)$$

the solution to equation (3) is:

$$\frac{1}{a^3}\left[\frac{1}{2} \times x^2 - 2bx - b^2 \ln x\right]\Big|_{r_1}^r = t \quad (4)$$

$h_{sf}$ = tissue latent heat of fusion
$\rho$ = density of tissue
$r$ = outer boundary spherical frozen zone
$t$ = time $$a = -\frac{k_f(T_\infty - T_i)}{h_{sf}\rho}$$

$$b = \frac{q}{4\pi h_{sf}\rho}$$

$$x = ar + b$$

As an example of the solution to a transient cooldown problem, we'll introduced the variables previously used in the evaluation of steady state performance plus $h_{sf} = 140$ BTU/lb, $\rho = 60$ lb/ft$^3$ and $q = 7.99$ BTU/hr (2.34 watts) into equation (4). The results are tabulated below.

| Typical Thermal Characteristics of Cryoprobe-Tip Tissue System During Cooldown Transient | | |
|---|---|---|
| r/r$_1$ | r(in) | t(min) |
| 1 | 0.04 | 0 |
| 2 | 0.08 | 0.06 |
| 5 | 0.20 | 1.02 |
| 10 | 0.40 | 20.91 |

The volume of frozen tissue approaches its ultimate steady state value asymptotically in time. In the case examined, 0.5 percent of the ultimate volume is frozen in 4 seconds, 8 percent in one minute and 67 percent in 20 minutes.

II. Thermodynamic Behavior of Cryogen Liquid Droplet/Carrier Gas Flow System

1. Temperature of Gas Returning in Annular Space 34

One objective of this invention is to have the exterior surface of the probe, except in the local region of the probe-tip, be near body temperature during a surgical procedure. In order to insure that this requirement is met requires the flow returning in the annular space 34 be near body temperature and this, in turn, requires a mass flowrate of warm carrier gas greatly in excess of the mass flowrate of the cryogen droplets as introduced in the cryoprobe head 72 and entering the central tube 18. The application of the first law of thermodynamics to the droplet/carrier gas flow system provides the means for establishing the design requirements.

$$m_{l1}h_{l1} + m_{g1}h_{g1} + q = (m_{l1} + m_{g1})h_{g3} \quad (1)$$

Equation (1) assumed complete evaporation of the liquid prior to reaching section 3 at the entrance to the annular space 34 and negligible heat input from the probe surroundings except at the probe-tip. (For identification of referenced system elements and flow sections see FIG. 2A).

$h_{g1}$ = enthalpy of carrier gas entering the central tube (flow section 1)
$h_{g3}$ = enthalpy of carrier gas in the annular space 34 (flow section 3)
$h_{l1}$ = enthalpy of the liquid cryogen droplets entering the central tube (flow section 1)
$m_{g1}$ = mass flowrate of carrier gas entering the central tube (flow section 1)
$m_{l1}$ = mass flowrate of liquid cryogen droplets entering the central tube (flow section 1)
$q$ = heat input at probe-tip Equation (1) can be rewritten in the form $$h_{l1} + \frac{m_{g1}}{m_{l1}}h_{g1} + \frac{q}{m_{l1}} = \left(1 + \frac{m_{g1}}{m_{l1}}\right)h_{g3} \quad (1a)$$

and also $$q/m_{l1} = (1 - f_e)h_{fg2} \quad (2)$$

$f_e$ = fraction of $m_{l1}$ evaporated during droplet travel to cold-tip end of central tube (flow section 2)
$h_{fg2}$ = latent heat of evaporation of liquid cryogen at flow conditions at probe-tip Combining equations (1a) and (2) gives:

$$h_{l1} + \frac{m_{g1}}{m_{l1}}h_{g1} + (1 - f_e)h_{fg2} = \left(1 + \frac{m_{g1}}{m_{l1}}\right)h_{g3} \quad (3)$$

As an example of the application of equation (3), we consider the case in which saturated liquid nitrogen droplets at one atmosphere are introduced as the cooling agent and warm gaseous nitrogen near body temperature is used as the carrier gas. Solutions to equation (3) for this droplet/carrier gas flow system appear in the table below.

| | | Temperature Decrease in Carrier Gas $T_{g1} - T_{g3}$ (R) | | |
|---|---|---|---|---|
| $f_e$ | $(1-f_e)h_{fg2}$(J/g) | $m_{g1}/m_{l1} = 25$ | $m_{g1}/m_{l1} = 50$ | $m_{g1}/m_{l1} = 100$ |
| 0 | 201.98 | 8.57 | 4.37 | 2.20 |
| 0.5 | 108.15 | 12.03 | 6.13 | 3.10 |
| 0.75 | 55.87 | 13.06 | 7.12 | 3.60 |
| 1.0 | 0 | 16.03 | 8.17 | 4.13 |

In order to meet the full heat extraction capability of the probe-tip q, the liquid droplet flow must be equal to:

$$m_{l1} = \frac{q}{(1 - f_e)(h_{fg2})} \quad (4)$$

A typical probe-tip may have a 0.08 inch diameter, an operating temperature of 80K and a heat extraction capability = 1.50 J/sec. Under these circumstances, the required flowrate of liquid nitrogen droplets are tabulated below.

| Required Flowrate of Liquid Nitrogen Cooling Agent | | |
|---|---|---|
| $f_e$ | $m_{l1}$(g/sec) | $m_{l1}$(lb/hr) |
| 0 | 7.43 × 10$^{-3}$ | 5.90 × 10$^{-2}$ |
| 0.5 | 1.39 × 10$^{-2}$ | 1.10 × 10$^{-1}$ |

-continued

Required Flowrate of Liquid Nitrogen Cooling Agent

| $f_e$ | $m_{l1}$(g/sec) | $m_{l1}$(lb/hr) |
|---|---|---|
| 0.75 | $2.68 \times 10^{-2}$ | $2.13 \times 10^{-1}$ |
| 1.0 | ∞ | ∞ |

The results of the above analyses show that the outside surface of the tubular probe can be maintained by practical means near body temperature. An optimized design would use a ratio $m_{g1}/m_{l1}$ equal to its smallest allowable value which is probably in the range of 25 to 50. In this way, the diameters of the conduits 18 and 20 that are required to carry the flow at an acceptable pressure level and pressure drop are minimized.

2. Pressure Drop In Liquid Cryogen Droplet/Carrier Gas Flow System

The gage pressure of the carrier gas introduced to the cryoprobe head is made equal to the allowable pressure drop in the liquid cryogen droplet/carrier flow system between the inlet to the central tube 18 to the exit of the annular space 34. However, to limit the adverse effect of increased droplet evaporation due to an accelerating flow in the central tube, it is advisable to limit the pressure drop in the central tube to about 25 percent of the average pressure of the flowing fluid in this tube.

The pressure drop in the flow traversing the length of the central tube is approximated by the equation $$\int_1^2 P dP = \frac{4fRTL}{2gD}\left(\frac{4m_{g1}}{\pi D^2}\right)^2 = \bar{P}\Delta P \quad (5)$$

Another form of equation (5) is:

$$\frac{\Delta P}{\bar{P}} = \frac{32fRTL}{\pi^2 gD^5 \bar{P}^2}(m_{g1})^2 \quad (5a)$$

D = internal diameter of center tube
f = friction factor appropriate to flow Reynold's number
L = length of center tube
$m_{g1}$ = mass flow rate of carrier gas
g = gravity constant
$\Delta P$ = pressure drop in flow traverse of center tube
$\bar{P}$ = average pressure of flowing fluids in center tube
 = $P_1 + P_2/2$
R = specific gas constant of flowing fluid
$\bar{T}$ = average temperature of flowing fluid in center tube As an example of the application of equation (5a), let $\Delta P/\bar{P} = 0.25$, R = 55.18 ft-lb/lb (appropriate to nitrogen gas, $\bar{T}$ = 559R, D = 0.04 in. and L = 48 in. With parameters, equation (5a) reduces to:

$$\bar{P} = 2.37 \times 10^6 m_{g1}\sqrt{f} \quad (5b)$$

In equation (5b), $\bar{P}$ is given in units of psia and $m_{g1}$ in units of lb/sec. Moreover, the flow Reynolds' numbers of design interest are in the range of $10^4$ to $10^5$ where the $\sqrt{f}$ is approximately equal to 0.084. The solution of equation (5a) gives results which are tabulated below in a range of parameters of interest to design needs.

Typical Average Pressure in Center Tube of a Cryosurgical Instrument Using the Two Phases of Nitrogen

| | $m_{g1}\left(\frac{lb}{sec} \times 10^3\right)$ | | | $\bar{P}$(psia) | |
|---|---|---|---|---|---|
| $f_e$ | $\frac{m_{l1}}{\left(\frac{lb}{sec} \times 10^5\right)}$ | $\frac{m_{g1}}{m_{l1}} = 25$ | $\frac{m_{g1}}{m_{l1}} = 50$ | $\frac{m_{g1}}{m_{l1}} = 25$ | $\frac{m_{g1}}{m_{l1}} = 50$ |
| 0.5 | 3.056 | 0.771 | 1.543 | 154 | 307 |
| 0.75 | 5.917 | 1.479 | 2.959 | 294 | 589 |

It is to be noted that the value of $\bar{P}$ is proportional to the rate of heat extraction at the cold-tip, to the internal diameter of the center tube to the −2.5 power and to the square root of the fluid temperature. For example, if the surgical procedure can be accomplished at a cold-tip temperature of −100F (360R) with a probe having an increase in the internal diameter of the center tube from 0.04 to 0.05 inches, the values of $\bar{P}$ appearing in the table are decreased by a factor of 2.8. Further, if the center tube length is reduced from 48 to 16 inches, the factor becomes 4.8.

III. Droplet Behavior

It is desirable to introduce cryogen droplets at the entrance of the central tube 18 in such a way that they meet the following criteria:

1. The liquid cryogen cooling agent should be introduced in the form of large droplets in order to minimize their evaporation during their passage to the cold-tip.

2. The relative velocity between the carrier gas and droplets at the central tube entrance should be made as small as practically possible also to minimize their evaporation during their passage to the cold-tip.

3. The liquid cryogen droplets arriving at the cold-tip should be large enough to insure that a predominant mass fraction impinge and are captured by the metal sponge 32.

4. An upper limit to the size of the liquid cryogen droplets that are introduced is set by the diameter of the inner tube. This limit, in typical cases, is about 1 mm.

It is known that a droplet having a size which will meet the criteria 1 through 4 above will not negotiate the expected curvilinear shapes assumed by the catheter-like tube system 14 without it impinging on the inner wall of the central tube. A good design evokes two known flow-heat transfer phenomena in order to limit the evaporation of the droplets that impinge on the central tube wall. First, and most important, is the well know Liedenfrost phenomenon in which a liquid droplet will sputter-off a much warmer surface with little evaporation. A common observation of this phenomenon is water drops dancing on a hot, oily frying pan surface. (The typical time of transit of droplets to the probe-tip is of the order of 0.03 seconds. Common observation indicates very little evaporation of "dancing droplets" occurs at times 100 times larger.) A plastic, non-wetting surface for the central tube enhances the benefits of this phenomenon. Of secondary importance, the circumstances of the two-phase, liquid-gas flow under consideration may be adjusted to preclude a stable annular liquid film at the wall and insure a dispersed (drop or mist) liquid regime even without heat transfer. Reference to the literature of two-phase flow shows that this latter condition is present marginally in designs dictated by other criteria.

1. Liquid Droplet Capture at Probe-Tip

The physical model for droplet impingement and capture is straightforward. With reference to FIG. 3, we note that the gas flow from the nozzle 46 at the distal end of the inner tube is made to turn 180 degrees to flow back into the annular space between the inner 18 and outer 20 tubes. The relatively large inertia of the droplets prevents them from following the gas streamlines and they continue their forward motion, impinge on the metal sponge 32 and are absorbed there. The ability of the droplets to follow the return flow streamlines depends on their diameters. The smaller diameter drops have a larger ratio of the drag force to inertia force acting on them and more faithfully follow the streamlines. The report of Dussourd, J. and Shapiro, A., "A Deceleration Probe for Measuring Stagnation Pressure and Velocity of a Particle Laden Gas Stream," N5 ori-07878, M.I.T. DIC 5-6985, May 1955, provides the means and data to get a quantitative measure of these effects.

The fraction of the drops which will impact the sponge of diameter D is designated the capture efficiency $\xi$. This efficiency is a function of two dimensionless variables.

$$\epsilon = \phi\left(\frac{3\rho_g D}{4\rho_l d}, \frac{\rho_g V_\infty d}{\mu_g}\right) \quad (1)$$

d = drop diameter
D = sponge target diameter
$V_\infty$ = velocity of approach of droplet cloud leaving nozzle
$\epsilon$ = capture efficiency
$\rho_g$ = carrier gas density
$\rho_l$ = density of cryogen liquid drop
$\mu_g$ = viscosity of carrier gas $$\frac{3\rho_g D}{4\rho_l d} = \text{"obedience" number}$$

$$\frac{\rho_g V_\infty d}{\mu_g} = \text{droplet Reynolds number}$$

By substituting parameters typical of those applying to a cryosurgical instrument employing the two phases of nitrogen, we find the data appearing in the cited reference predicts a capture efficiency of 99 percent for a particle size of 100 microns and a capture efficiency of 90 percent for a particle size of 20 microns. The data of the cited reference is based on a model of the cloud of drops approaching the target disk that flow through the projected area of the disk far upstream of it. Those drops that flow close to the centerline of the disk have a much higher capture efficiency than the average for the cloud. Accordingly, the actual capture efficiency of droplets in our design system is higher than those values given above.

2. Droplet Generation

A number of correlations are available to predict the size of liquid drops produced by various methods. The *Handbook of Aerosols*, published by TIC, ERDA, 1976 provides a good summary of these correlations as well as some test data. However, the atomization process is incompletely understood and the various correlations tend to be relatively unique to the system under investigation. In short, predictions of drop size based on the various correlations predict drop size with a large uncertainty band and tests on the system of interest are required if more precise information is needed. In the case of the preferred system for cryogen droplet production, see FIG. 5, adjustments are built into the design to allow emperical determination of the optimum drop size.

Two methods are of most interest to this invention:

1) a pressurized liquid jet atomizer in which drops are produced by injecting the liquid into a quiescent gas and 2) a gas pressurized atomizer in which a relatively high velocity gas stream is made to flow over a low velocity jet of liquid. The physical basis for each of these methods is the same. The relative velocity between the gas and liquid flows establish viscous shear effects which act to break the liquid into filaments and by subsequent instability phenomena into drops The preferred system for cryogen droplet production set forth in this invention is of the gas atomization type. Other potential droplet production methods that have been cited are of the pressurized liquid type.

Figure 9:
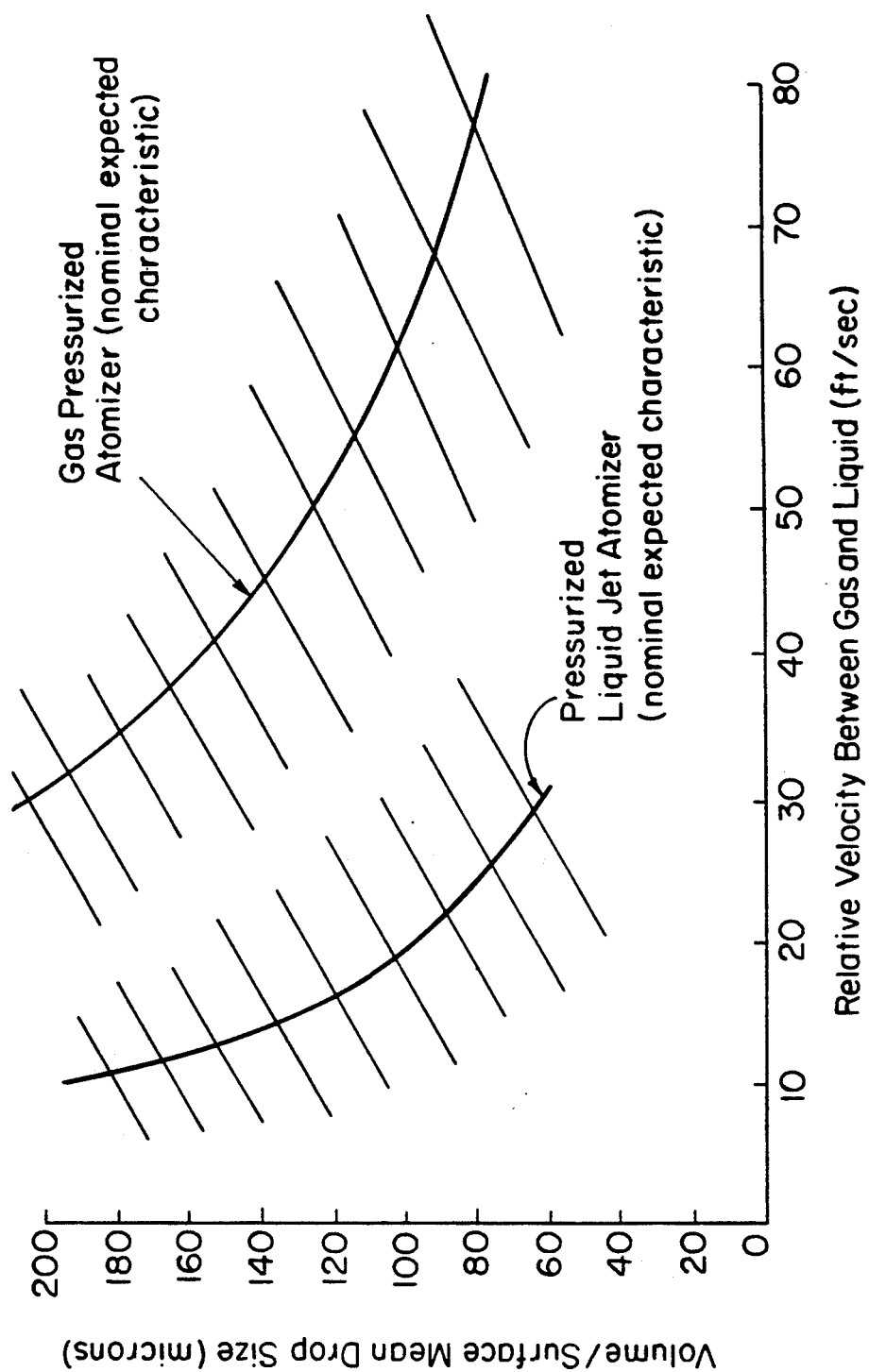
FIG. 9 is a plot of droplet size relative to relative velocity for two atomizer types referenced in the theoretical discussion.

The droplet size predicted by correlations for each of the atomizer types is illustrated in FIG. 9. The Nukiyama-Tanasawa correlation was used for the gas pressure type of atomizer and one of many was used for the pressurized liquid jet atomizer. The important point to be made is that the relative velocity between the gas and liquid streams in the local region where they first come in contact can be used to control the drop size produced.

3. Droplet Heat Transfer

The fractional amount of liquid that is evaporated, $f_e$, in the passage of the droplets down the center tube 18 to their ultimate capture in the metal sponge 32 should be limited in a practical instrument design to something less than about 75 percent. Unfortunately, the physical processes which combine to determine $f_e$ are interrelated and complex but enough is known about them to get a good analytical prediction. In subsequent discussion, the preferred embodiment of a cryosurgical instrument which utilizes liquid nitrogen droplets in a warm nitrogen carrier gas is assumed.

First one notes that the temperature of the newly atomized liquid drops are at a temperature below the saturation temperature corresponding to the pressure of the carrier gas. Because of this fact, the carrier gas will very quickly condense on the initially produced drops until the drop temperature is raised to its equilibrium value. The fractional increase in droplet mass due to condensation depends on the pressure of the carrier gas stream. Fractional droplet mass increases of 14, 23 and 44 percent correspond to carrier gas pressures of 150, 300 and 600 psia, respectively. Next, because the temperature of the carrier gas is much warmer than the droplets, a combined heat and mass transfer process takes place in which heat is transferred to the droplet causing evaporation and the mass flow of nitrogen vapor away from it. Further, the rate of heat transfer to the droplet, or the evaporation rate, depends on the drop size and the relative velocity between the drop and the surrounding gas. The relative velocity at any location (and time) in the drop's travel, in turn, depends on the history of its velocity and size up to this location.

The solution to this complex problem involves the introduction of known correlations for forced-convective heat transfer to a sphere (such as the commonly used Ranz-Marshall correlation) modified to take account of evaporation. In addition, it involves relationships between the drag coefficient of a sphere and its Reynolds number based on the relative gas/liquid drop velocity from which the drop acceleration at any time and location can be determined. Analytical expressions for the physical processes outlined above have been derived and a method of solution has been devised which, for a given initial drop size, predicts the drop size at the distal end of the center tube.

Some results from calculated solutions to the analytical system outlined above have been made under the droplet dynamic, gas dynamic, and thermodynamic circumstances that have been established in prior elements of this "Theoretical Basis" section to be best suited to the operational and design requirements of the instrument. These results show that the initial drop size has the most significant influence on the value of $f_e$ and, additionally, introduce no problems in respect to meeting other design criteria. Overall these analytical results establish a design—useful, but approximate, equation:

$$f_e = 3000\, d^{-1.6} \tag{2}$$

The values of $f_e$ for a relatively small center tube length of 16 inches are about 45 percent of those for a length of 4 feet. The units for the droplet diameter d appearing in equation (2) is microns. Some solutions to equation (2) are presented in the table below.

The Fraction of Droplet Mass Evaporated vs. Initial Drop Diameter

| Initial Drop Diameter, d (microns) | $f_e$ L = 48 in. | $f_e$ L = 16 in. |
|---|---|---|
| 170 | 0.81 | 0.36 |
| 200 | 0.62 | 0.28 |
| 250 | 0.47 | 0.21 |
| 300 | 0.33 | 0.15 |

The results presented in the table above provide a guide to the range of drop sizes that should be produced by the atomizer. According to the tabulated results, the larger the initial drop size the better. However, an upper bound on the practical limits on drop size are set by other considerations such as the internal diameter of the center tube (which may typically be equal to 1000 microns) and the droplet size distribution. Additional evaporation due to droplet contact with the wall of the center tube is reasoned to be small due to the Liedenfrost effect as discussed in a prior paragraph.

In summary, we expect that an atomization method that produces volume/surface mean drop sizes in the range of 200 to 300 microns will result in instrument performance best suited to meet the operational needs of surgical procedures. However, any good instrument design should incorporate means to vary the drop size and observe (test) the effects on the overall performance of the surgical instrument before fixing its final configuration. The surgical instrument proposed by this invention provides this means.

IV. Options for Optimum Combinations of Working Fluids

All analyses relative to the design and operation of this invention have been based on the use of liquid nitrogen droplets as the cooling agent transported in a carrier gas of warm gaseous nitrogen. The question arises are there other combinations of liquid and gas better suited to the cryosurgical needs of the instrument. In order to answer this question we need a basic criterion that will serve to screen candidate working fluids. The basic criterion of choice is the outside diameter of instruments having the same length, cooling capacity, etc. The working fluid combinations are ranked on the ability to minimize the outside diameter of the instrument subject to a number of constraints, as follows:

a) The hemispherical tip must be sized to meet the design heat extraction rate.

b) The hemispherical tip must operate at a range of design temperatures (probably below 190K) which establishes the saturation temperature of the condensate at the probe tip.

c) The carrier gas cooling must be limited to a small specified amount.

d) The pressure of the carrier gas must be limited to a specified safe amount.

e) The pressure drop in the inner carrier gas stream leading to the instrument tip must be limited to a specified fraction of its average pressure.

f) The working fluids must not be flammable or toxic.

Items a) and b) are established by the medical procedures and the thermophysical properties of the tissue to be treated. Item c) is also established by medical considerations—the amount that the temperature of the body tissue can be lowered and the duration of subnormal temperature that can be allowed without permanent damage. Item d) is established in order to conform to the stress limits of the carrier gas conducts. Item e) is established in order to limit the carrier gas acceleration and, hence, droplet heat transfer and evaporation. Item f) is dictated by safety standards.

An equation for the inner diameter of the center tube D, as dependent on the physical properties of the liquid cooling agent and the carrier gas has been developed to serve as the means for ranking candidate working fluids. The outside diameter of the cryoprobe tube system 14 is a fixed multiple of D, the multiplying factor being approximately 2. This screening equation was produced by combining the several basic equations which relate the design and performance characteristics of the proposed cryosurgical instrument: 1) the momentum equation applied to the carrier gas flow in the center tube as constrained by the allowable limits on $\Delta P/\bar{P}$ and $\bar{P}$, 2) the energy equation applied to the carrier gas and droplet vapor flow as constrained by the allowable temperature decrease in this flow $\Delta T_{13}$, and 3) the heat transfer and droplet dynamic equation which determine the droplet evaporation. Somewhat simplified versions of these equations were used to facilitate the process of combination without involving approximations unacceptable to the screening purpose.

The properties of the working fluids that enter the equation set outlined above are as follows:

$C_p$=specific heat of carrier gas at constant pressure
$H_{fg}$=latent heat of liquid cooling agent (drops)
k=coefficient of thermal conductivity of the carrier gas M.W. = molecular weight of carrier gas
$T_\infty - T_l$ = body temperature minus liquid drop temperature
$\rho_l$ = density of liquid drop The properties of the system which are considered fixed are:
$d_o$ = initial diameter of drop
f = coefficient of friction appropriate to flow in center tube
g = gravity constant
= length of center tube
$\overline{P}$ = allowable mean pressure of carrier gas flowing in center tube $\Delta P/\overline{P}$=allowable fractional pressure drop in flow of carrier gas down center tube q=heat extraction rate at probe-tip R=universal gas constant $T_\infty$=average temperature of carrier gas flow equal to body temperature $\Delta T_{13}$=allowable decrease in temperature of carrier gas flow A final equation for screening candidate working fluids that results from the analytical operations outlined is given below.

$$D = \frac{A^{0.2}}{C_p^{0.4} M.W^{0.2}[1 - A^{0.4}B(kc_p^{0.2}M.W.^{0.6}(T_\infty - T_1)/\rho_1 h_{fg}]^{1.2}} \quad (1)$$

where:

$$A = \frac{32fLq^2TR}{\pi^2 g \Delta T_{13} P^2 \Delta P/P}$$

$$B = \frac{1.5\pi LP\Delta T_{13}}{d_o^2 RTq}$$

Assuming the following values as constraints on the application: $d_o$=200 microns, f=0.007, L=4 ft., $\overline{P}$=150 psia, $\Delta P/\overline{P}$=0.25, q=1 watt and $\overline{T}$=559 the screening equation reduces to:

$$D = \frac{2.205 \times 10^{-3}}{C_p^{0.4} M.W^{0.2}[1 - 29.24kc_p^{0.2}M.W.^{0.6}(T_\infty - T_1)/\rho_1 h_{fg}} \quad (1a)$$

The system of units to be used for the properties in equation (1*a*) is ft., °F., BTU, hr. and $lb_m$. By selecting promising working fluid candidates and introducing their properties into equation (1*a*), it has been found that liquid nitrogen droplets with a warm gaseous nitrogen as the carrier appears as a superior design choice. The use of liquid methane droplets and warm gaseous helium for the carrier is predicted to give about the same value for the internal diameter of the center tube, but, of course, this combination would be ruled out due to safety considerations.

The invention claimed is:

1. A cryogenic apparatus comprising:

a coolant means for producing cryogenic droplets entrained in a carrier gas, the carrier gas being at a temperature warm enough to be non-injurious to living tissue, and a probe comprising a cold-tip for cooling contacted objects and an elongated probe housing having a distal end closed by the cold-tip and a proximal end coupled to the coolant means such that the carrier gas passes through the probe housing, the entrained cryogenic droplets being transported by the carrier gas to the distal end of the probe where the droplets are deposited for cooling the cold-tip

2. A cryogenic apparatus as claimed in claim 1 wherein the probe housing is formed of a flexible, substantially tubular material.

3. A cryogenic apparatus as claimed in claim 1 wherein an outer surface of the probe housing is near body temperature during operation.

4. A cryogenic apparatus as claimed in claim 1 wherein the probe has an outer diameter of about 2 mm or less.

5. A cryogenic apparatus as claimed in claim 1 wherein the probe has a flexible length of up to about four feet.

6. A cryogenic apparatus as claimed in claim 1 wherein the probe housing further comprises an inlet tube positioned concentrically within an outlet tube, the inlet tube being coupled to the coolant system for passing the entrained cryogenic droplets disposed in the carrier gas to the distal end of the probe, the outlet tube subsequently passing carrier gas through an annular region between the inlet and outlet tubes to the proximal end of the probe for discharge into atmosphere.

7. A cryogenic apparatus as claimed in claim 6 wherein the inlet tubes are near body temperature during operation.

8. A cryogenic apparatus as claimed in claim 6 wherein the carrier gas passing through the annular region between the inlet and outlet tubes is near body temperature.

9. A cryogenic apparatus as claimed in claim 6 wherein the probe housing further comprises an external tube surrounding the inlet and outlet tubes and connected to the cold-tip, the external tube being formed of a low-thermal conductivity material for thermally isolating the inlet and outlet tubes and the cold-tip.

10. A cryogenic apparatus as claimed in claim 1 wherein the cold-tip comprises a head formed of a thermally conductive material for freezing contacted objects and a porous heat sink being in thermal contact with the head, the porous heat sink storing the entrained cryogenic droplets transported by the carrier gas for cooling the head.

11. A cryogenic apparatus as claimed in claim 10 wherein the porous heat sink is formed of a thermally conductive material shaped in a stepped-cone configuration for providing a variable thermal resistance heat flow path to the head.

12. A cryogenic apparatus as a claimed in claim 1 wherein the coolant means comprises:

a housing having an inlet port for receiving the carrier gas having a first temperature and pressure and an outlet port coupled to the probe housing; and a condenser extending into the housing and having an outer surface exposed to the carrier gas, the outer surface of the condenser having a second temperature being less than the saturation temperature of the carrier gas such that a cryogenic liquid condensate forms on the outer surface, the condenser having a distal end being shaped such that the cryogenic liquid condensate drains off the distal end as entrained cryogenic droplets, the distal end of the condenser being positioned relative to an inlet nozzle of the outlet port such that the entrained cryogenic droplets are further atomized to a desired drop size and are transported in the carrier gas from the housing via the outlet port.

13. A cryogenic apparatus as claimed in claim 12 wherein the coolant means further comprises a heater coil connected to the condenser for producing a thermal gradient along the outer surface of the condenser to control the rate of production of the cryogenic liquid condensate.

14. A cryogenic apparatus as claimed in claim 13 further comprising a temperature sensor embedded in the cold-tip and providing a signal for controlling electric power to the heater coil to produce a preprogrammed cold-tip temperature versus time profile.

15. A cryogenic apparatus as claimed in claim 12 wherein the condenser is a hollow thermally conductive post filled with cryogenic liquid.

16. A cryogenic apparatus as claimed in claim 15 wherein the cryogenic liquid is stored in an attached dewar and gravity fed into the post.

17. A cryogenic apparatus as claimed in claim 1 wherein the probe is adapted for use in surgical procedures.

18. A cryogenic apparatus as claimed in claim 1 wherein the coolant means comprises a pressurized liquid/gas jet atomizer.

19. A cryogenic apparatus as claimed in claim 1 wherein the coolant means comprises a sonic-augmented pressured liquid/gas jet atomizer.

20. A cryogenic apparatus as claimed in claim 1 wherein the cryogenic droplets have a volume-surface means droplet diameter of approximately 200 microns.

21. A cryogenic apparatus as claimed in claim 1 wherein the cryogenic droplets have a volume-surface mean diameter ranging between 170–300 microns.

22. A cryogenic apparatus comprising:
a coolant means for producing cryogenic droplets entrained in a carrier gas, the coolant means comprising:
  a housing having an inlet port for receiving the carrier gas having a first temperature and pressure and an outlet port coupled to the probe housing; and
  a condenser extending into the housing and having an outer surface exposed to the carrier gas, the outer surface of the condenser having a second temperature being less than the saturation temperature of the carrier gas such that a cryogenic liquid condensate forms on the outer surface, the condenser having a distal end being shaped such that the cryogenic liquid condensate drains off the distal end as entrained cryogenic droplets, the distal end of the condenser being positioned relative to an inlet nozzle of the outlet port such that the entrained cryogenic droplets are transported in the carrier gas from the housing via the outlet port; and
a probe comprising a cold-tip for cooling contained objects and an elongated probe housing having a distal end closed by the cold-tip and a proximal end coupled to the coolant means such that the carrier gas passed through the probe housing, the entrained cryogenic droplets being transported by the carrier gas to their distal end of the probe where the droplets are deposited for cooling the tip.

23. A cryogenic apparatus comprising:
a coolant means for producing cryogenic droplets entrained in a carrier gas, the coolant means comprising:
  a housing having an inlet port for receiving the carrier gas having a first temperature and pressure and an outlet port coupled to the probe housing;
  a condenser extending into the housing and having an outer surface disposed to the carrier gas, the outer surface of the condenser having a second temperature being less than the saturation temperature of the carrier gas such that a cryogenic liquid condensate forms on the outer surface, the condenser having a distal end being shaped such that the cryogenic liquid condensate drains off the distal end as entrained cryogenic droplets, the distal end of the condenser being positioned relative to an inlet nozzle of the outlet port such that the entrained cryogenic droplets are further atomized to a desired drop size and are transported in the carrier gas from the housing via the outlet port; and
  a heater coil connected to the condenser for producing a thermal gradient along the outer surface of the condenser to control the rate of production of the cryogenic liquid condensate; and
a probe comprising a cold-tip for cooling contacted objects and an elongated probe housing having a distal end closed by the cold-tip and a proximal end coupled to the coolant means such that the carrier gas passes through the probe housing, the entrained cryogenic droplets being transported by the carrier gas to their distal end of the probe where the droplets are deposited for cooling the tip.

24. A cryogenic apparatus comprising:
a coolant means for producing cryogenic droplets entrained in a carrier gas, the coolant means comprising;
  a housing having an inlet port for receiving the carrier gas having a first temperature and pressure and an outlet port coupled to the probe housing;
  a condenser extending into the housing and having an outer surface disposed to the carrier gas, the outer surface of the condenser having a second temperature being less than the saturation temperature of the carrier gas such that a cryogenic liquid condensate forms on the outer surface, the condenser having a distal end being shaped such that the cryogenic liquid condensate drains off the distal end as entrained cryogenic droplets, the distal end of the condenser being positioned relative to an inlet nozzle of the outlet port such that the entrained cryogenic droplets are further atomized to a desired drop size and are transported in the carrier gas from the housing via the outlet port; and
  a heater coil connected to the condenses for producing a thermal gradient along the outer surface of the condenser to control the rate of production of the cryogenic liquid condensate;
a probe comprising a cold-tip for cooling contacted objects and an elongated probe housing having a distal end closed by the cold-tip and a proximal end coupled to the coolant means such that the carrier gas passed through the probe housing, the entrained cryogenic droplets being transported by the carrier gas to the distal end of the probe where the droplets are deposited for cooling the cold-tip; and
a temperature sensor embedded in the cold-tip and providing a signal for controlling electric power to the heater coil to produce a preprogrammed cold-tip temperature versus time profile.

* * * * *

UNITED STATES PATENT AND TRADEMARK OFFICE
CERTIFICATE OF CORRECTION

PATENT NO. : 5,324,286
DATED : June 28, 1994
INVENTOR(S) : Arthur A. Fowle

It is certified that error appears in the above-identified patent and that said Letters Patent is hereby corrected as shown below:

column 9, line 61, before "Probe-Tip" insert --I.--.

In Claim 1, column 20, line 4, after "cold-tip" insert --.--.

In Claim 7, column 20, line 28, after "inlet" insert --and outlet--.

In Claim 12, column 20, line 52, after "as" delete "a".

In Claim 20, column 21, line 30, change "means" to --mean--.

In Claim 21, column 21, line 31, change "claim 1" to --claim 20--.

In Claim 22, column 21, line 55, change "contained" to --contacted--; at line 59, change "passed" to --passes-- at line 61, change "their" to --the-- and at line 63, change "tip" to --cold-tip--.

In Claim 23, column 22, line 4, change "disposed" to --exposed--; at line 27, change "their" to --the-- and at line 28, change "tip" to --cold-tip--.

UNITED STATES PATENT AND TRADEMARK OFFICE
CERTIFICATE OF CORRECTION

PATENT NO. : 5,324,286

DATED : June 28, 1994

INVENTOR(S) : Arthur A. Fowle

It is certified that error appears in the above-identified patent and that said Letters Patent is hereby corrected as shown below:

In Claim 24, column 22, line 37, change "disposed" to --exposed--; at line 52, change "condenses" to --condenser-- and at line 59, change "passed" to --passes--.

Signed and Sealed this

Thirteenth Day of September, 1994

Attest:

BRUCE LEHMAN

Attesting Officer    Commissioner of Patents and Trademarks